(12) United States Patent
Layne et al.

(10) Patent No.: US 8,092,480 B2
(45) Date of Patent: Jan. 10, 2012

(54) PLATFORM CANNULA FOR GUIDING THE EXPANSION OF EXPANDABLE BODIES AND METHOD OF USE

(75) Inventors: Richard W. Layne, Palo Alto, CA (US); Robert M. Scribner, Los Altos, CA (US); Christopher R Ralph, Mountain View, CA (US)

(73) Assignee: Kyphon SARL, Neuchatel (CH)

( * ) Notice: Subject to any disclaimer, the term of this patent is extended or adjusted under 35 U.S.C. 154(b) by 199 days.

(21) Appl. No.: 09/828,470

(22) Filed: Apr. 6, 2001

(65) Prior Publication Data

US 2002/0026195 A1 Feb. 28, 2002

Related U.S. Application Data

(60) Provisional application No. 60/195,207, filed on Apr. 7, 2000, now abandoned.

(51) Int. Cl.
*A61M 29/00* (2006.01)

(52) U.S. Cl. ................ 606/192; 606/86 R

(58) Field of Classification Search ........... 623/17.12, 623/11.11, 17.11, 17.19, 7, 8; 606/91–95, 606/86, 80, 99, 90, 193, 194, 192, 198, 98, 606/60, 61, 191; 604/264, 285, 912, 918, 604/921

See application file for complete search history.

(56) References Cited

U.S. PATENT DOCUMENTS

| | | |
|---|---|---|
| 3,557,794 A | 1/1971 | Van Patten |
| 3,837,347 A | 9/1974 | Tower |
| 4,083,369 A | 4/1978 | Sinnreich |
| 4,147,169 A * | 4/1979 | Taylor ............... 604/102.02 |
| 4,205,683 A | 6/1980 | O'Neill |
| 4,217,903 A * | 8/1980 | Witherow ............ 604/102.03 |
| 4,240,433 A | 12/1980 | Bordow |
| 4,313,434 A | 2/1982 | Segal |
| 4,315,512 A | 2/1982 | Fogarty |
| 4,327,709 A | 5/1982 | Hanson et al. |
| 4,327,736 A | 5/1982 | Inoue |
| 4,346,698 A | 8/1982 | Hanson et al. |
| 4,494,535 A | 1/1985 | Haig |
| 4,842,585 A | 6/1989 | Witt |
| 4,969,888 A | 11/1990 | Scholten et al. |
| 5,074,871 A | 12/1991 | Groshong |
| 5,100,390 A | 3/1992 | Lubeck et al. |
| 5,102,413 A * | 4/1992 | Poddar .................. 606/62 |
| 5,108,404 A | 4/1992 | Scholten et al. |
| 5,112,310 A | 5/1992 | Grobe |
| 5,116,305 A | 5/1992 | Milder et al. |

(Continued)

FOREIGN PATENT DOCUMENTS

JP 8038618 2/1996

(Continued)

*Primary Examiner* — Patricia M Bianco
*Assistant Examiner* — Camtu T Nguyen

(57) ABSTRACT

This invention relates to devices, such as cannulas or needles, which are used for inserting expandable structures, such as medical balloons, into interior regions of a human or animal body, as well as methods for their use. In various embodiments, insertion devices described herein are capable of flaring at their tip to ease insertion and removal of expandable structures and reduce the risk of damaging such expandable structures during their insertion, inflation and removal. In other embodiments, insertion devices described herein are capable of directionally guiding and/or inhibiting expansion of an expandable structure within an interior region of an animal or human body to create optimally placed cavities for repair, augmentation and/or treatment of fractured and/or diseased bone.

1 Claim, 17 Drawing Sheets

U.S. PATENT DOCUMENTS

| | | | |
|---|---|---|---|
| 5,176,683 A | 1/1993 | Kimsey et al. | |
| 5,254,091 A | 10/1993 | Aliahmad | |
| 5,359,995 A | 11/1994 | Sewell, Jr. | |
| 5,380,290 A | 1/1995 | Makower et al. | |
| 5,411,509 A | 5/1995 | Hilal | |
| 5,423,850 A | 6/1995 | Berger | |
| 5,439,447 A | 8/1995 | Miraki | |
| 5,456,267 A | 10/1995 | Stark | |
| 5,456,667 A | 10/1995 | Ham et al. | |
| 5,467,786 A | 11/1995 | Allen et al. | |
| 5,545,136 A * | 8/1996 | Berger | 604/96.01 |
| 5,601,590 A | 2/1997 | Bonutti | |
| 5,788,703 A * | 8/1998 | Mittelmeier et al. | 606/94 |
| 5,792,044 A * | 8/1998 | Foley et al. | 600/114 |
| 5,817,074 A | 10/1998 | Racz | |
| 5,827,289 A * | 10/1998 | Reiley et al. | 606/86 |
| 5,849,014 A * | 12/1998 | Mastrorio et al. | 606/94 |
| 5,865,728 A | 2/1999 | Moll et al. | |
| 5,882,340 A | 3/1999 | Yoon | |
| 5,928,162 A | 7/1999 | Giurtino et al. | |
| 5,961,499 A | 10/1999 | Bonutti et al. | |
| 5,972,015 A | 10/1999 | Scribner et al. | |
| 5,976,105 A | 11/1999 | Marcove et al. | |
| 6,036,682 A | 3/2000 | Lange et al. | |
| 6,036,711 A | 3/2000 | Mozdzierz et al. | |
| 6,048,346 A | 4/2000 | Reiley et al. | |
| 6,066,154 A | 5/2000 | Reiley et al. | |
| 6,241,734 B1 | 6/2001 | Scribner et al. | |
| 6,248,110 B1 | 6/2001 | Reiley et al. | |
| 6,280,456 B1 | 8/2001 | Scribner et al. | |
| 6,350,252 B2 | 2/2002 | Ray et al. | |
| 6,423,083 B2 | 7/2002 | Reiley et al. | |
| 6,440,138 B1 | 8/2002 | Reiley et al. | |
| 6,468,279 B1 | 10/2002 | Reo | |
| 6,488,653 B1 | 12/2002 | Lombardo | |
| 6,582,446 B1 * | 6/2003 | Marchosky | 606/167 |
| 6,607,544 B1 | 8/2003 | Boucher et al. | |
| 6,675,665 B2 | 1/2004 | Blazquez Navarro et al. | |
| 6,706,069 B2 * | 3/2004 | Berger | 623/17.12 |
| 7,214,178 B2 | 5/2007 | Lubock | |
| 2002/0010472 A1 * | 1/2002 | Kuslich et al. | 606/93 |
| 2002/0032447 A1 * | 3/2002 | Weikel et al. | 606/86 |
| 2002/0072768 A1 | 6/2002 | Ginn | |
| 2002/0099385 A1 * | 7/2002 | Ralph et al. | 606/92 |
| 2003/0050702 A1 | 3/2003 | Berger | |
| 2003/0130664 A1 | 7/2003 | Boucher et al. | |

FOREIGN PATENT DOCUMENTS

| | | |
|---|---|---|
| WO | WO 97/28840 | 8/1997 |
| WO | 9856301 | 12/1998 |
| WO | WO 98/56301 | 12/1998 |
| WO | WO 99/02214 | 1/1999 |
| WO | WO 99/37212 | 7/1999 |
| WO | WO 99/62416 | 12/1999 |
| WO | WO 00/09024 | 2/2000 |
| WO | WO 01/76492 | 10/2001 |
| WO | WO 01/76514 | 10/2001 |

* cited by examiner

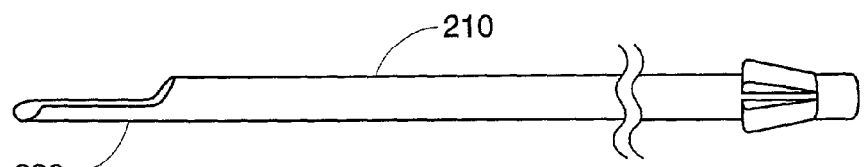
Fig. 7
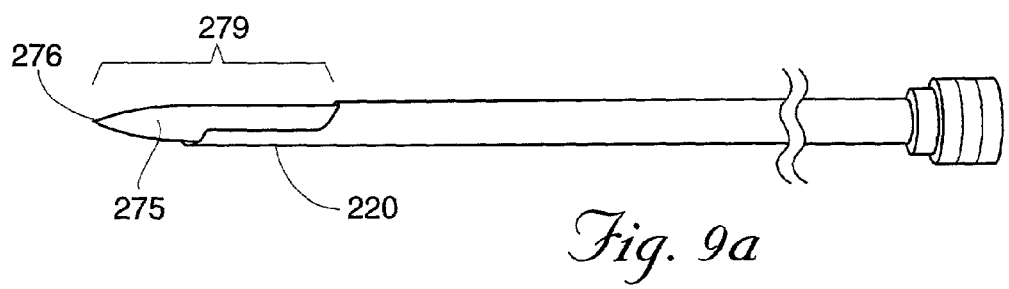
Fig. 9a
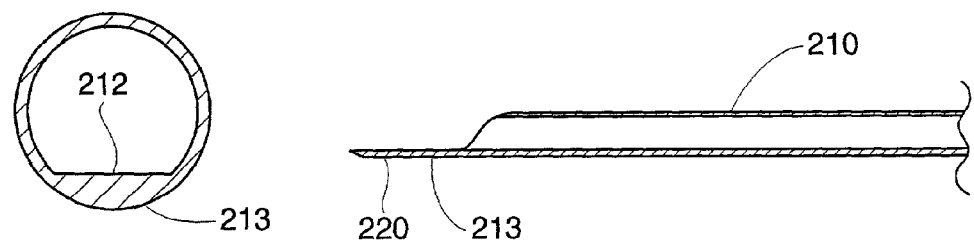
Fig. 10
Fig. 11
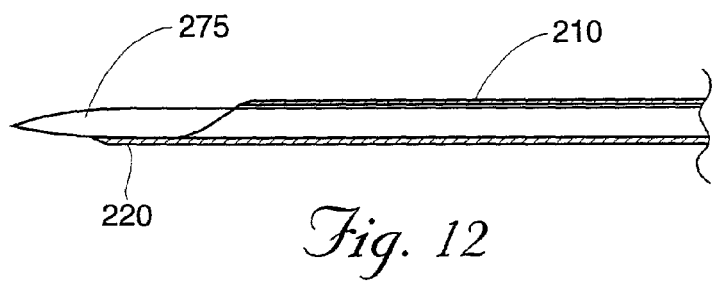
Fig. 12
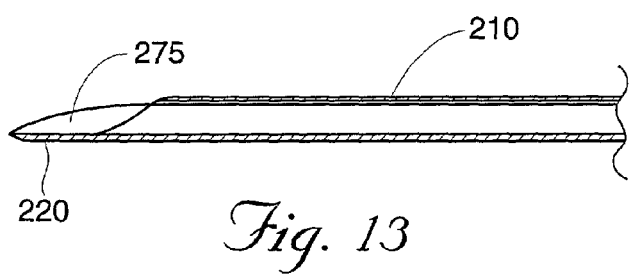
Fig. 13

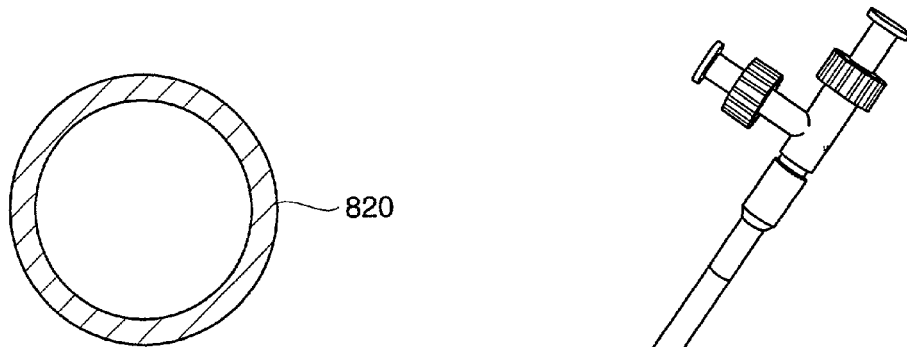
Fig. 35
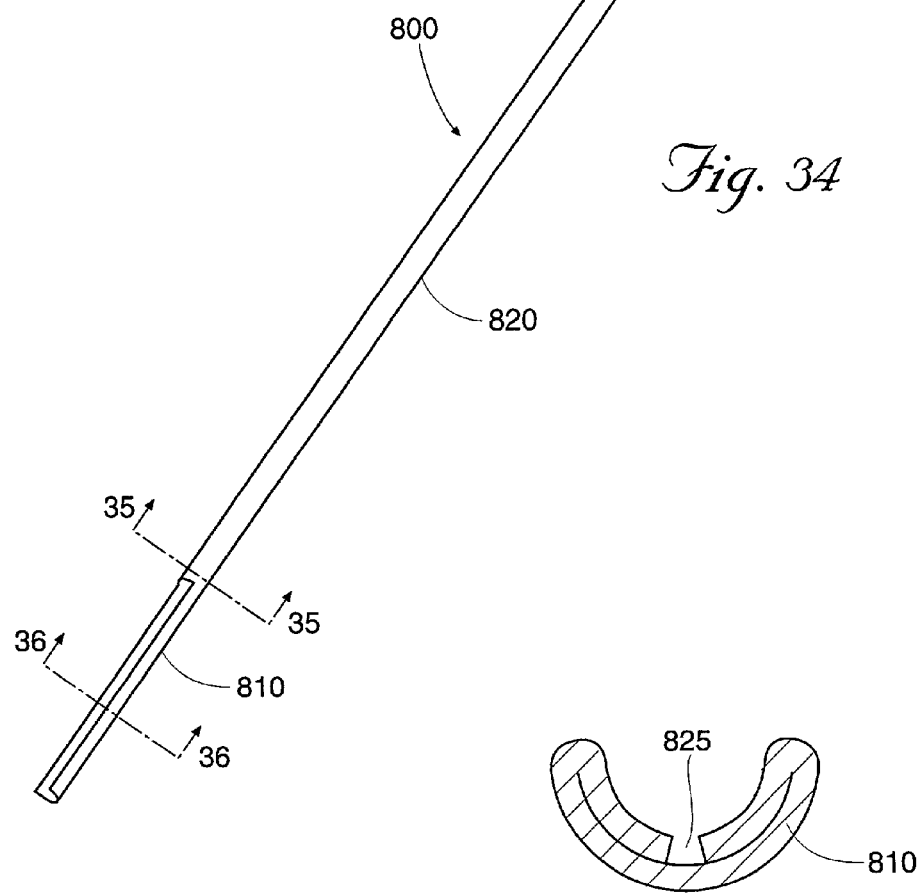
Fig. 34
Fig. 36

PLATFORM CANNULA FOR GUIDING THE EXPANSION OF EXPANDABLE BODIES AND METHOD OF USE

CROSS-REFERENCE TO RELATED APPLICATION

The present application is a non-provisional of provisional application No. 60/195,207, filed on Apr. 7, 2000, now abandoned.

FIELD OF THE INVENTION

This invention relates to an insertion device which is capable of guiding expansion of an expandable structure towards or away from a desired direction and/or interior region of an animal or human body. This invention further relates to an insertion device for inserting expandable structures, such as medical balloons, into an interior region of a human or animal body, wherein the device is capable of expanding at the tip. The present invention also relates to methods of using the disclosed devices in the repair, augmentation and/or treatment of fractured and/or diseased bone.

BACKGROUND OF THE INVENTION

Expandable structures, such as balloon dissectors and catheters, are used in various surgical procedures and for various rehabilitative purposes in the medical arts. In angioplasty, balloon catheters are commonly inserted into veins and arteries to expand blood vessels, most commonly to dilate and/or remove obstructions in the blood vessel (e.g. to remove constrictions blocking blood vessels which can cause a heart attack or stroke). Other types of surgical balloons have been used to aid surgeons in accessing specific organs during surgery, usually in lieu of previous insufflation techniques. Such balloons are commonly inserted in a deflated state through an insertion device comprising a cannula, catheter tube, or other similar device, and are positioned under an organ. The balloon may then be inflated to lift and separate a desired organ away from surrounding organs and tissue to make sides of the desired organ easier to access during surgery. The balloon may also be placed and inflated so as to lift and separate other organs and tissues, leaving the desired organ for surgery exposed beneath.

Medical balloons have also been used during procedures for repairing and/or reinforcing fractured and/or diseased bones. Some physicians have used such balloons to create a working space adjacent fractured and/or diseased bone to allow the installation of plates, screws and/or other implantable articles to the bone. In this type of procedure, a cannula is generally inserted through an incision in the skin near the fracture area. A balloon is then inserted through the cannula and inflated between the bone and surrounding tissue around the fracture site to create a working space. A support plate and bone screws, or other similar implements, can then be installed at the fracture site through small incisions in the skin. This type of procedure allows a surgeon to install implantable articles without having to make a long skin incision to isolate and expose the bone.

More recently, balloons have been employed inside fractured and/or diseased bones to repair, reinforce and/or treat the bone. In these procedures, balloons can be inserted through a cannula and inflated inside the bone, which can compact cancellous bone, create a cavity and move cortical bone. The cavity can be filled with a suitable bone filler, such as bone cement (e.g., polymethylmethacrylate—PMMA), autograft or allograft tissue, or various other bone substitutes. When the bone filler hardens, it essentially creates an internal "cast" which allows the bone to heal properly, but also desirably allows the bone to bear weight immediately.

SUMMARY OF THE INVENTION

The present invention provides insertion devices which may be used with an expandable structure such as a balloon catheter to direct the expansion of the structure toward or away from a desired direction. Directed expansion of the expandable structure provides the physician with significant control over the compression of cancellous bone and creation of cavities within the bone, as well as control over the movement of cortical bone. In addition, the controlled expansion of an expandable structure allows the physician to tailor the shape and dimensions of the cavity, and the resulting shape and dimensions of the bolus of filler material contained therein. Moreover, directed expansion of an expandable structure permits a physician to minimize disruption of healthy cancellous and/or cortical bone during a treatment procedure, thereby further enhancing healing of the bone after treatment. Accordingly, the devices and methods disclosed herein permit the physician to optimize the ability of the bone to withstand compressive forces and/or heal as quickly as possible after the procedure is completed.

Expandable structures such as balloon catheters and dissectors are typically formed in spherical or elliptical shapes, and normally expand substantially outward. These balloons are desirably fairly low-profile such that they can fit through a cannula. Once inserted through the cannula into the region of treatment, such balloons will generally inflate fairly symmetrically about the axis of the cannula or other insertion device. However, as discussed in U.S. Pat. No. 5,972,015, which is incorporated by reference herein, inflation of a balloon about the cannula's axis can be undesirable in some situations. To account for these situations, various alternative balloon designs and expansion constraint arrangements have been proposed, such as those described in the '015 patent.

The inventions disclosed herein further permit a practitioner to utilize a wide variety of expandable structures in conjunction with the methods and devices disclosed herein. Because the cannula or other insertion device substantially guides the direction of expansion of the expandable structure, there is less need to incorporate expansion constraints in the expandable structure itself. In addition, if the insertion device is comprised of a radiopaque material, the orientation of the device itself can be visualized during the surgical procedure under x-ray fluoroscopy, allowing the practitioner to visually verify the direction of expansion of the structure throughout the entire procedure. Of course, it should be understood that the devices and methods of the present invention could also be used in conjunction with expandable structures incorporating various expansion restraint arrangements.

In a general embodiment of the present invention, an insertion device comprises a hollow member, which is preferably cylindrical, with a distal end and a proximal end, wherein the distal end is the tip, or point of insertion, of the insertion device. The distal end of the hollow member desirably comprises a platform which constrains expansion of the expandable structure in one or more directions, but permits the expandable structure to expand in non-constrained directions. In effect, the platform of the hollow member acts as a support or foundation against which the expandable structure pushes as it expands. Desirably, the supporting action of the platform induces the expandable structure to expand away from the platform, allowing the practitioner to direct expansion towards and/or away from a desired region.

In another general embodiment, the platform comprises a platform or expansion guide which is inserted through a hollow member of an insertion device, the guide desirably extending distally past the tip of the hollow member and into a bone. The guide will desirably act as a support or foundation against which the expandable structure expands, inducing the structure to expand away from the guide. Because this embodiment of the guide travels through the hollow member, and need not initially penetrate soft tissues and/or the harder cortical bone, the guide design can be optimized to provide maximum support for the expandable structure.

In another general embodiment of the present invention, an insertion device comprises a hollow member with a distal end and a proximal end, wherein the distal end is the tip, or point of insertion, of the insertion device. The distal end of the hollow member desirably comprises a platform which directs the expansion of the expandable structure in one or more directions. The distal end of the hollow member further comprises one or more crease or fold lines along which at least a portion of the platform desirably deforms after insertion into a bone. By deforming along predetermined lines, sharp surfaces on the platform are desirably moved away from the expandable structure. In addition, bending of the platform can significantly affect the surface area of the platform in contact with the expandable structure as well as the strength and resistance to deformation of the platform. After the expandable structure is contracted, the platform can be withdrawn through the cannula, with the distal end of the insertion device desirably bending the platform towards a lower-profile shape for removal.

In another general embodiment of the present invention, the insertion device comprises a hollow member having a plurality of score lines spaced about the circumference of the distal tip, these score lines desirably forming a plurality of adjacent sections oriented in a first, lower profile orientation. After inserted to a desired location within the vertebral body, the adjacent sections can be expanded outward to a second orientation, where the adjacent sections substantially form a funnel, cone or flare at the tip of the insertion device. When removal of the expandable structure is desired, the flared tip desirably guides the expandable structure into the cannula, facilitating passage of the expandable structure into and through the cannula. If desired, the adjacent sections can further incorporate one or more guides or ribs which desirably impinge upon the expandable structure, folding and/or twisting the expandable structure along desired lines and/or in a desired manner, further facilitating removal of the expandable structure through the cannula. When removal of the insertion device from the vertebral body is desired, the withdrawal of the insertion device through the harder cortical bone desirably bends the adjacent sections back towards and/or into their first, lower profile orientation.

The present invention is further related to methods for using the disclosed devices for repair, augmentation and/or treatment of fractured and/or diseased bones. One embodiment of an insertion device constructed in accordance with the teachings of the present invention is inserted through cortical bone and into cancellous bone in a vertebral body of a patient. The insertion device is positioned such that the platform directs the expansion of an expandable structure towards a section of cortical bone to be moved to a desired position, such as a depressed upper or lower plate of a vertebral body. The expandable structure is expanded against the platform, which desirably induces the expandable structure to expand substantially away from the platform, compressing cancellous bone to form a cavity and moving the targeted section of cortical body towards a desired position. The expandable structure is contracted, and the cavity is then filled with an appropriate bone filler material. This method, which permits manipulation of cortical bone with a minimum of cancellous bone compression, allows a practitioner to move targeted cortical bone while preserving much of the cancellous bone in an uncompressed state. In addition, this method permits the practitioner to maximize the force which the expandable structure exerts on the cortical bone.

In another embodiment of the present invention, an insertion device constructed in accordance with the teachings of the present invention is inserted into cancellous bone in a vertebral body of a patient. The insertion device is positioned such that the platform directs the expansion of an expandable structure towards a section of cancellous bone to be compressed. The expandable structure is expanded, which desirably compresses some or all of the targeted cancellous bone, creating a cavity within the cancellous bone. The expandable structure is contracted and, if desired, the insertion device is repositioned such that the platform directs the expansion of an expandable structure towards another section of cancellous bone to be compressed. The expandable structure is expanded, compressing some or all of the targeted cancellous bone and increasing the size and/or altering the shape of the cavity within the bone. If desired, the procedure can be repeated to create a cavity of desired dimensions. The cavity is then filled with an appropriate bone filler material. This method, which facilitates the creation of large cavities within the bone, allows the practitioner to tailor the cavity shape/size to optimize the post-treatment strength and/or healing of the bone. Similarly, the disclosed method can be used to reposition cortical bone towards a desired position, permitting a practitioner to gradually displace small or large sections of the cortical bone, at the practitioner's option.

In another embodiment, the disclosed devices and methods facilitate a practitioner's ability to repair, reinforce and/or treat targeted bone regions in situations where the insertion device is initially positioned near a cortical bone wall of a targeted bone region. Because the disclosed devices and methods provide substantial control over the direction of expansion of the expandable structure, the practitioner can position and/or reposition the platform to shield the nearby cortical bone from some or all of the expandable structure during some or all of the surgical procedure. Depending upon the orientation of the platform, the structure can be expanded to differing dimensions, desirably maximizing compression of cancellous bone and/or movement of cortical bone at each orientation. Accordingly, there is no need to reorient the entire insertion device to accomplish the objectives of the procedure, which desirably eliminates a source of additional trauma occurring during the procedure.

In another embodiment, an insertion device is inserted through cortical bone and into cancellous bone in a vertebral body of a patient. A stylet in the insertion device is removed, causing the distal end of the hollow member of the insertion device to expand or flare. An expandable structure is inserted through the insertion device into the vertebra, is expanded to create a cavity, and is contracted and removed through the insertion device. As the expandable structure is withdrawn through the insertion device, the flared distal end of the insertion device desirably guides the structure into the insertion device. The cavity is then filled with an appropriate bone filler.

Other objects, advantages and embodiments of the invention are set forth in part in the description which follows, and in part, will be obvious from this description, or may be learned from the practice of the invention.

BRIEF DESCRIPTION OF THE DRAWINGS

FIG. 7 is a side view of another alternate embodiment of an insertion device constructed in accordance with the teachings of the present invention, the device comprising an extension or platform extending from the distal end of the device;

FIG. 9a is a side view of another alternate embodiment of an insertion device constructed in accordance with the teachings of the present invention with a stylet positioned within the lumen of the device;

FIG. 10 is an end view of another alternate embodiment of an insertion device constructed in accordance with an alternate embodiment of the present invention;

FIG. 11 is a side view of the insertion device of FIG. 10.

FIG. 12 is a side view of the insertion device of FIG. 10, with a stylet positioned within the hollow member of the device;

FIG. 13 is a side view of an alternate embodiment of an insertion device constructed in accordance with the teachings of the present invention, with a stylet positioned within the hollow member of the device;

FIG. 34 is a side view of another alternate embodiment of an insertion device constructed in accordance with an alternate embodiment of the present invention;

FIG. 35 is a cross-sectional view of the insertion device of FIG. 34, taken along line 35-35;

FIG. 36 is a cross-sectional view of the insertion device of FIG. 34, taken along line 36-36;

DETAILED DESCRIPTION OF PREFERRED EMBODIMENTS

The present invention overcomes the problems and disadvantages associated with current strategies and designs in insertion devices for use with expandable structures, such as medical balloons. In particular, the present invention provides insertion devices which may be used with expandable structures to direct expansion of the structure as well as to assist in insertion and removal of expandable structures from an interior region of a human or animal body. The methods and instruments suitable for such treatment are more fully described in U.S. Pat. Nos. 4,969,888, 5,108,404, 5,827,289, 5,972,015, 6,048,346 and 6,066,154, each of which are incorporated herein by reference.

Figure 1:
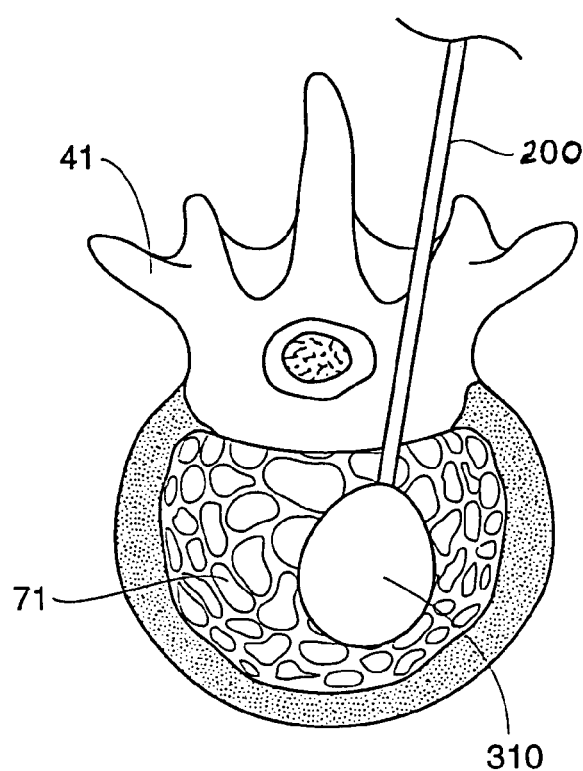
FIG. 1 is a coronal view of a vertebral body, showing a cannula inserted in a vertebral body, with a spherical expandable structure expanded within the vertebral body.

FIG. 1 depicts a vertebra 41 to be treated using an expandable structure 310. An insertion device 200, such as a cannula or spinal needle, extends through the cortical bone 69 of the vertebra 41, and into the cancellous bone 71. An expandable structure 310 is introduced into the vertebra 41 through the insertion device 200, and desirably expands within the cancellous bone 71, typically expanding outward in a spherical, cylindrical or other manner thereby creating a cavity. To avoid contacting the cortical bone 69 during expansion of the structure 310, a practitioner will typically position the insertion device 200 a sufficient distance away from the cortical bone 69 to allow room for the structure 310 to expand outward. However, if the insertion device 200 is positioned too close to the cortical bone 69, if the structure expands a greater amount towards the cortical bone 69 (such a where the cancellous bone is weaker in that direction), or if the intervening anatomy severely constrains placement of the insertion device to locations near the cortical bone 69, the expansion of the structure and cavity creation may be less than optimal.

Figure 2:
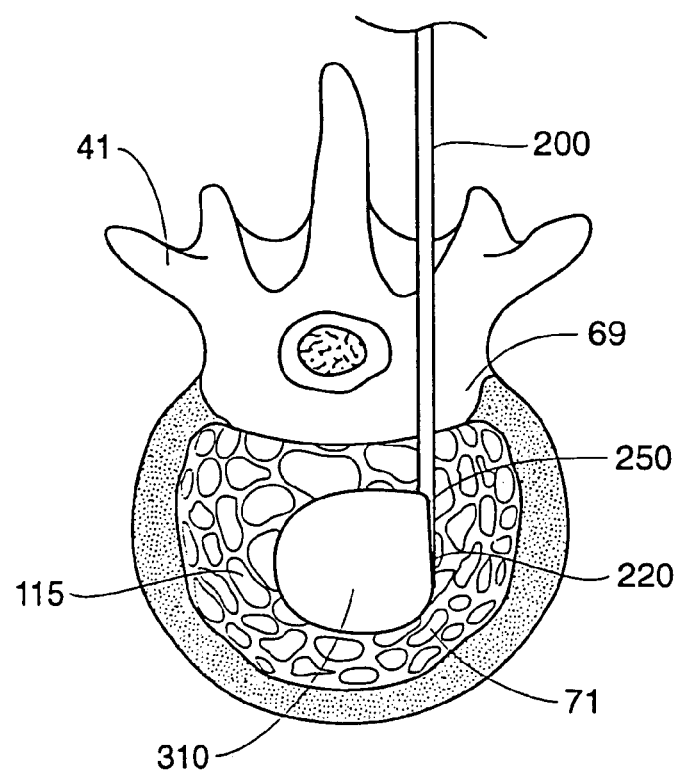
FIG. 2 is a coronal view of a vertebral body, showing one embodiment of an insertion device constructed in accordance with the teachings of the present invention which has been inserted into a vertebral body, with an expandable structure expanded within the vertebral body.

FIGS. 2 and 7 depict one embodiment of an insertion device constructed in accordance with the teachings of the present invention. The insertion device comprises a hollow member 210 which may be any appropriate shape, but is preferably cylindrical. The hollow member 210 has a distal end 250 and a proximal end 255, wherein the distal end 250 is the tip, or point of insertion, of the insertion device. The hollow member 210 may be any appropriate length to allow the insertion device to provide percutaneous access to an interior region of a body requiring treatment. In one preferred embodiment, the hollow member 210 is approximately 12 cm long.

The hollow member 210 has an appropriate central bore diameter and wall thickness to allow surgical instruments and/or medical materials to be passed therethrough, while desirably being strong enough to resist deformation during insertion into an interior region of a body such as a bone. In a preferred embodiment, the hollow member 210 has an internal bore diameter of 0.3 cm and a wall thickness of 0.05 cm. The hollow member 210 may further be made of any material which is appropriate for use within a human or animal body including, but not limited to, stainless surgical steel, teflon, polyethylene, polypropylene, silicates, and liquid crystal polymers (as described in U.S. Pat. No. 6,036,711, which is incorporated herein by reference). In one preferred embodiment, the hollow member 210 is made of stainless steel. If desired, the hollow member 210 may further be coated with any appropriate medical grade coating including, but not limited to, an anti-infective, an anticoagulant, a release coating, and/or a slipping agent.

Figure 28:
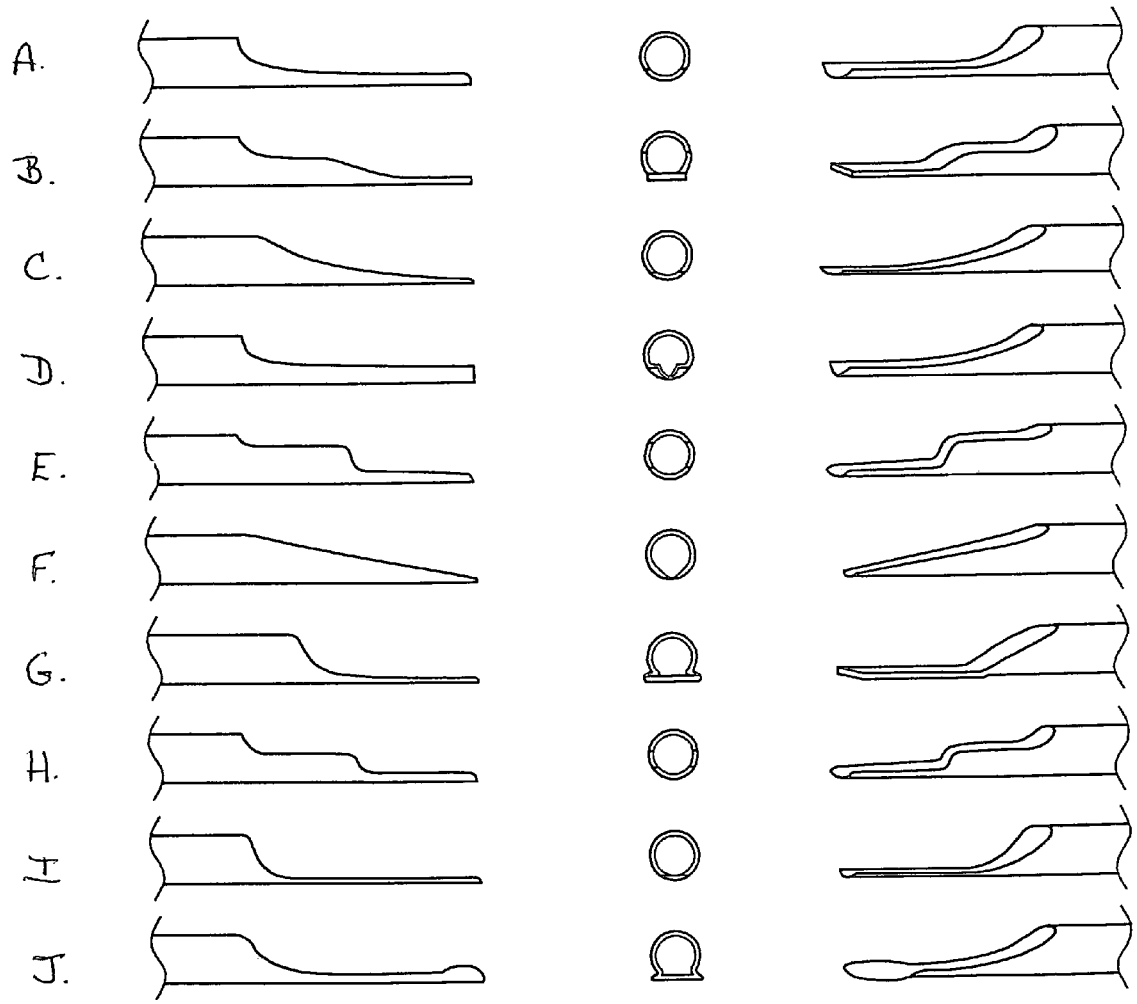
FIG. 28 are side and perspective views of various embodiments of platforms constructed in accordance with the teachings of the present invention.

In one embodiment, an extension or platform 220 protrudes from the distal end 250 of the hollow member 210. In this embodiment, the platform 220 comprises a semi-cylindrical section which extends from the walls of the hollow member 210. Of course, the platform could be formed in many different configurations, including one or more of those shown in FIG. 28. In one preferred embodiment, the platform 220 is made of the same material as the hollow member 210. Of course, it should be understood that the platform 220 could be formed of and/or coated with materials different from those incorporated into the hollow member 210. In addition, the platform 220 could be formed integrally with the hollow member 210, such as by cutting away a portion of the hollow member 210 near the distal tip 250 and leaving a cradle shape, or by attaching the platform 220 to the distal tip 250 of the hollow member by various means well known in the art such as welding, adhesive bonding, etc. In one embodiment, the platform 220 will have sufficient column strength such that it will not buckle and/or significantly deform as the insertion device is introduced through soft tissue and/or the bone. In the disclosed embodiment, the portion of the distal tip 250 of the hollow member 210 has been longitudinally bisected and removed, with the remaining semi-cylindrical section comprising the platform 220.

Desirably, the platform 220 will be positioned near the expandable structure 310 prior to expansion, with the platform 220 located between the expandable structure 310 and a region within the vertebra 41 which is not to be compressed or affected. As the structure 310 expands, the platform 220 will act as a support, foundation or barrier to the expandable structure 310, inhibiting the structure 310 from expanding in one or more directions. In effect, the platform 220 will induce the expandable structure 310 to expand away from the platform 220. Because the insertion device and platform 220 are substantially secured within the cortical bone, the platform 220 will desirably remain substantially rigid and/or immobile within the vertebra as the structure expands. This arrangement allows a practitioner to direct the expansion of the expandable structure 310 towards or away from a specific region of the vertebra.

Figure 8:
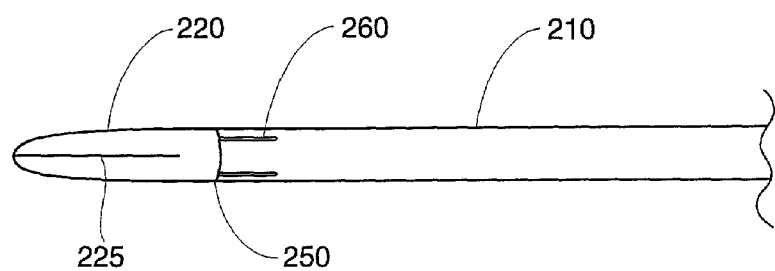
FIG. 8 is a top plan view of another alternate embodiment of an insertion device constructed in accordance with the teachings of the present invention, showing a crease line extending along a platform of the device.
Figure 14:
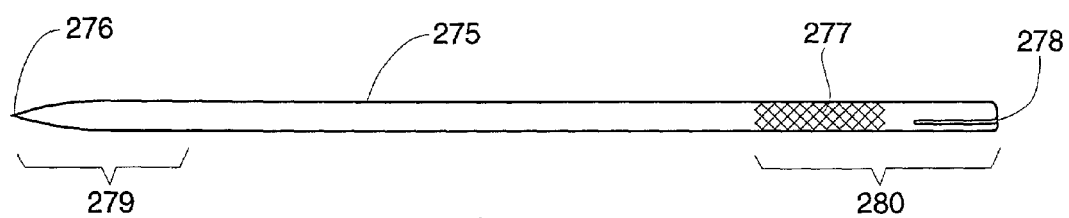
FIG. 14 is a side view of one embodiment of a stylet constructed in accordance with the teachings of the present invention, for use with various embodiments of the insertion device of the present invention.

In another embodiment, best shown in FIG. 8, the platform 220 comprises at least one longitudinal crease line 225, preferably located near the center of the platform, along which at least a portion of the platform 220 desirably deforms prior to, during or after expansion of the structure 310. By causing the platform 220 to deform in a controlled manner, this embodiment facilitates introduction of the platform in a lower profile condition, permits the platform to deform to a larger area to best direct the expansion of the structure, and then allows the platform to be withdrawn in a lower profile condition. As an expandable structure 310 is expanded, thereby exerting pressure against the platform 220, the crease line 225 facilitates flattening of the platform 220 in a controlled manner, thereby providing a widened and improved support surface for guiding expansion of the expandable structure 310. Flattening of the support 220 can also deform outward the edges of the platform 220, which may be sharp, thereby reducing the risk of damaging or rupturing the expandable structure 310. The crease lines 225 may be created by mechanical cutting, laser etching, welding, brazing, or any other well known means.

In an alternate embodiment, the crease line 225 could reinforce the platform 220, minimizing deformation of the platform 220 during expansion of the structure 220. For example, the rounded underside of the platform 220 could be crimped or bent along the longitudinal axis of the platform to stiffen the platform 220 and resist deformation of this type. If desired, the crimp (not shown) could parallel one or more crease lines 225. In an alternate embodiment, a crimp (not shown) which extends approximately 7 mm proximally from the distal tip of the platform 220 results in a significant increase in the resistance of the platform 220 to displacement and/or deformation.

In another alternative embodiment, the distal tip of the platform incorporates one or more serrations or teeth which extend outward from the distal tip and facilitate anchoring of the platform into the opposing cortical wall of the targeted bone region. This arrangement, which allows the platform to be supported at both ends, significantly increases the resistance of the platform to displacement and/or deformation during expansion of the expandable structure.

In another embodiment, best shown in FIGS. 11, 12 and 13, the platform 220 comprises a relatively flat section extending from the distal end 250 of the hollow member 210. In a preferred embodiment, the platform 220 can incorporate a flattened top surface 212 and a curved outer surface 213, the curved outer surface 213 being formed integrally with the hollow member 210. Although this embodiment slightly constricts the inside bore of the hollow member 210, the shape and increased thickness of the platform 220 greatly increase the amount of force the platform 220 can withstand without deforming. In addition, this embodiment minimizes impingement of sharp edges onto the expandable structure. Moreover, the flat and thickened platform 220, as shown in FIG. 13, can be shaped to have a sharpened tip so that the platform 220 can easily pass through soft tissue and/or bone. In an alternate embodiment, a flexible and/or pliable surface (not shown) may be positioned between the expandable structure and/or the platform, or may be incorporated into the platform or expandable structure, to minimize tearing, cutting and/or other failure of the expandable structure.

Figure 29:
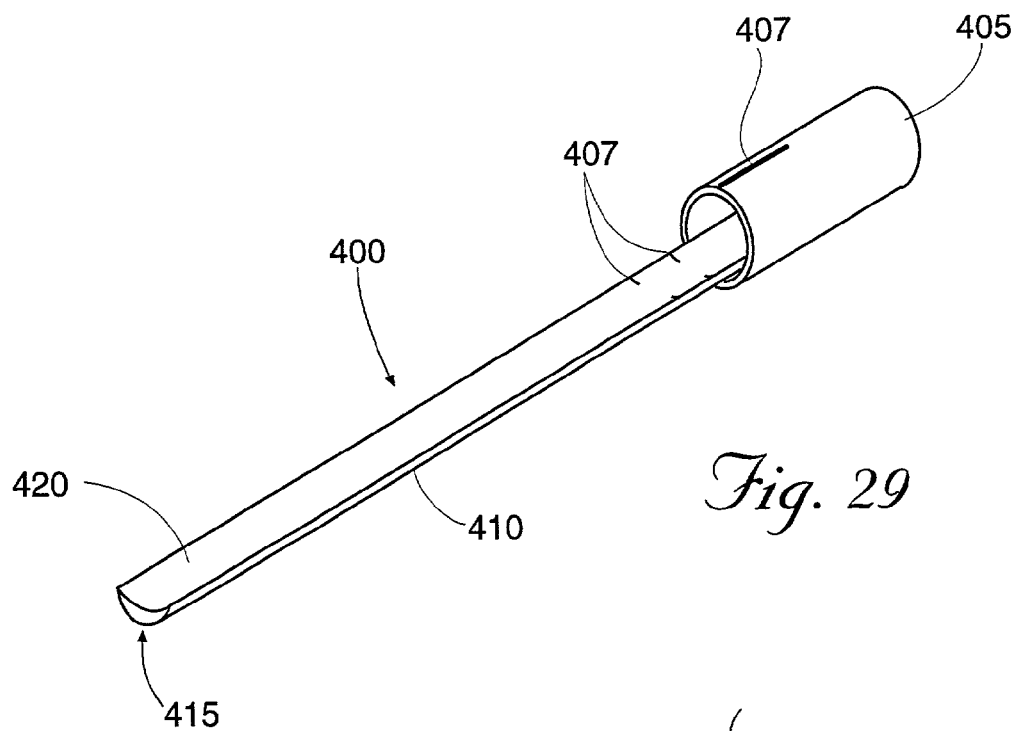
FIG. 29 is a side perspective view of one embodiment of an expansion guide constructed in accordance with the teachings of the present invention.
Figure 30:
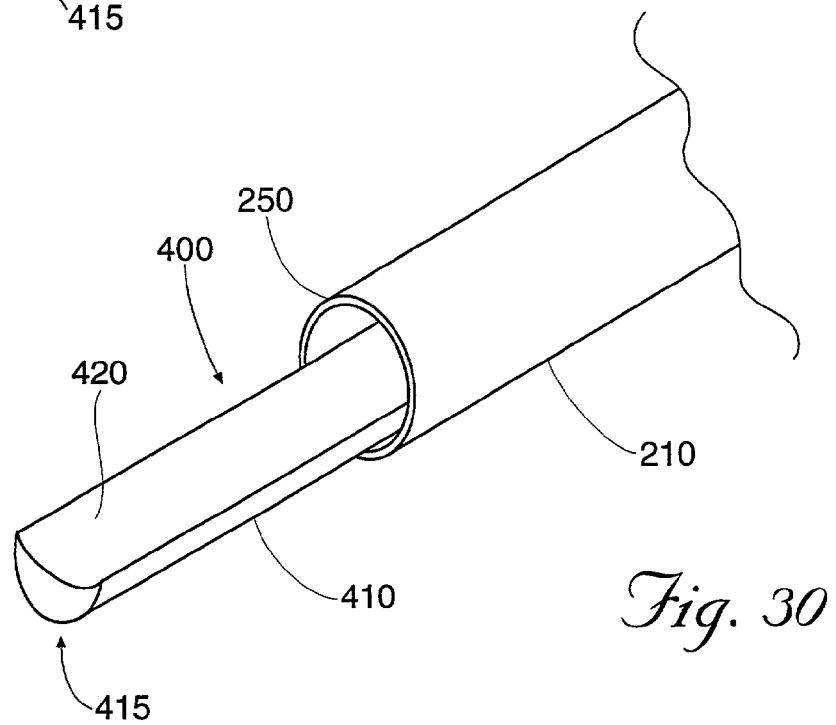
FIG. 30 is a partial side perspective view of the expansion guide of FIG. 29 inserted into an insertion device.

FIGS. 29 and 30 depict an alternate embodiment of an insertion device and associated component constructed in accordance with the teachings of the present invention. In this embodiment, the insertion device or cannula comprises a hollow member 210 which may be any appropriate shape, but is preferably cylindrical. The hollow member 210 has a distal end 250, wherein the distal end 250 is the tip, or point of insertion, of the insertion device. An expansion guide 400, best shown in FIG. 29, comprises a handle assembly 405 and a guide shaft 410. The guide shaft 410 is desirably longer than hollow member 210, and is also desirably sized to pass through the lumen of the hollow member 210. In the disclosed embodiment, an upper surface 420 of the guide shaft 410 is desirably substantially flattened, and a lower surface 415 of the guide shaft is curved. If desired, the handle assembly 405 and/or guide shaft 410 can incorporate one or more alignment marks 407 to indicate the orientation of the guide shaft, as well as the amount the guide shaft extends from the distal end 250 of the hollow member. In addition, the handle assembly may incorporate mechanical connectors or clips (not shown) to secure the expansion guide 400 to the hollow member 210.

In this embodiment, after an insertion device is positioned within a targeted vertebral body, the expansion guide 400 can be positioned near an expandable structure (not shown) prior to expansion, with the guide shaft 410 located between the expandable structure and an area of the cancellous bone where compression of the cancellous bone is not desired. If desired, the expandable structure can be introduced through the insertion device before the expansion guide 400 is introduced through the insertion device. As the structure expands, the guide shaft 410 will act as a support, foundation or barrier to the expandable structure, desirably inhibiting the structure from expanding in one or more directions. In effect, the guide shaft 410 will act similar to the platform 220 previously described, and will induce the expandable structure 310 to expand away from the guide shaft 410. This arrangement allows a practitioner to direct the expansion of the expandable structure towards or away from a specific region of the vertebral body. In addition, because the expansion guide 400 can be inserted to varying depths within the hollow member, the practitioner can choose the desired length of the guide shaft 410 to extend out of the insertion device. In an alternate embodiment, if desired a plurality of platforms (not shown) can be used to shield multiple directions.

Because the expansion guide 400 may be introduced after the insertion device is already positioned within the targeted vertebral body, the expansion guide 400 need not have sufficient column strength to penetrate soft tissue and/or cortical bone. This allows the expansion guide 400 to assume a variety of cross sectional forms, including one or more of the forms shown in FIG. 28.

Figure 3A:
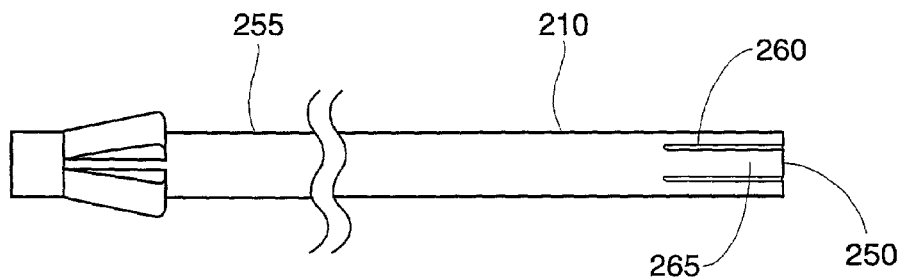
FIG. 3a is a side view of an alternate embodiment of an insertion device constructed in accordance with the teachings of the present invention, wherein the distal end of the hollow member comprises one or more longitudinal score lines at its circumference.
Figure 4:
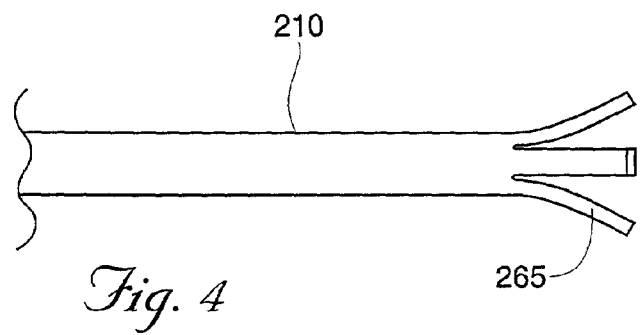
FIG. 4 is a side view of the insertion device of FIG. 3a, showing the adjacent sections in a deployed or flared position.
Figure 6:
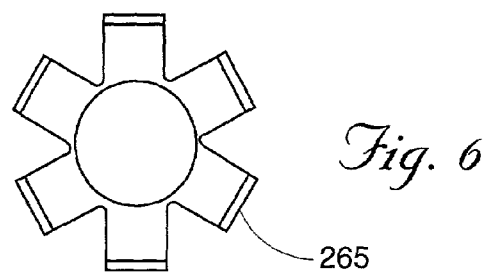
FIG. 6 is an end of the insertion device of FIG. 4.

In another alternate embodiment of an insertion device constructed in accordance with the teachings of the present invention, best shown in FIGS. 3a, 4 and 6, the insertion device comprises a cylindrical hollow member 210 having a distal end 250 and a proximal end 255, wherein the distal end 250 is the tip, or point of insertion, of the insertion device. The distal end 250 of the hollow member 210 is scored longitudinally to form a plurality of score lines 260 around the circumference of the hollow member 210. The plurality of score lines 260 may run parallel or at an angle to one another, and are separated by adjacent sections 265. The score lines 260 may be of any appropriate length and depth to allow the distal end 250 to flare (See FIGS. 4 and 6) when an outward pressure is exerted upon the adjacent sections 265.

In one preferred embodiment, the score lines 260 extend approximately 0.5 cm along the longitudinal axis of the hollow member 210, and extend through the wall of the hollow member 210. The score lines 260 are cut into the distal end 250 using any appropriate technique known to those of skill in the art including, but not limited to, laser cutting or etching, chemical etching and/or mechanical cutting with carbide or diamond tip saws or high pressure water. The distal end 250 of the hollow member 210 will desirably comprise a sufficient number of longitudinal score lines 260 to allow ease of flaring of the distal end 250. The quantity of score lines 260 required for appropriate flaring is determined by the diameter and wall thickness of the hollow member 210 and the ductility of the material. In one embodiment of the present invention, the hollow member 210 comprises at least three score lines 260 in the distal end 250. In another embodiment, best shown in FIG. 6, the hollow member 210 comprises six score lines 260 in the distal end 250.

The flaring of the tip of the hollow member 210 may ease insertion and removal of an expandable structure, such as a medical balloon. By flaring the tip, the sharp outer edges of the hollow member 210 are pushed away from the expandable structure and into the surrounding cancellous bone. The expandable structure is thus isolated from these sharp edges, which could contact the expandable structure during expansion, possibly causing the structure to rupture or tear. During withdrawal of the expandable structure, the larger diameter of the flared tip will desirably guide the expandable structure into the smaller diameter hollow member 210, easing withdrawal of the expandable structure into and through the hollow member 210.

If desired, flaring of the tip can be accomplished using an expandable structure to provide a desired outward force, or the tip can be flared mechanically. For example, in the embodiment shown in FIG. 3b, the adjacent sections 265 are thickened on their internal surfaces to form one or more protrusions 266 extending inward from each adjacent section 265. If desired, the protrusions 266 could be formed as a single continuous thicker area of the circumference of distal end 250, interrupted by the longitudinal score lines 260. When a tool, such as a blunt obturator, boring member or stylet 275, which is described below, slides across or presses against the protrusions 266, the adjacent sections 265 are desirably forced outward, flaring the distal end 250 of the hollow member 210 in the desired manner.

Figure 15:
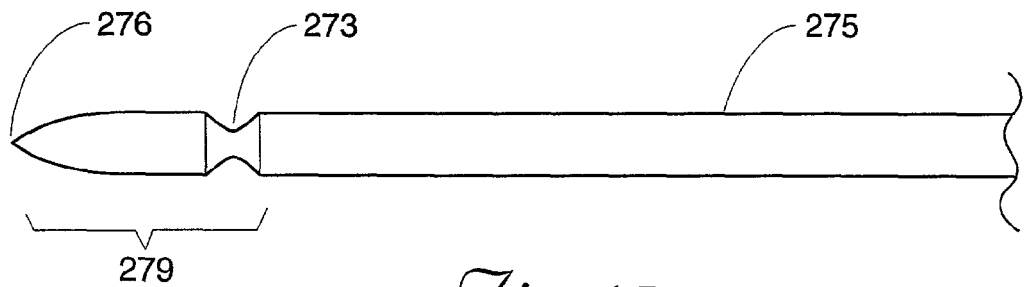
FIG. 15 is a side view of an alternate embodiment of a stylet constructed in accordance with the teachings of the present invention, for use with alternate embodiments of the insertion device of the present invention.
Figure 16A:
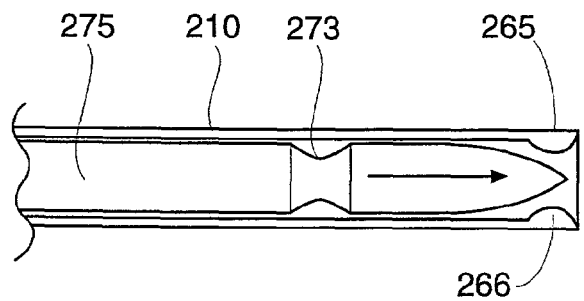
FIG. 16a is a cross sectional side view of an alternate embodiment of an insertion device and stylet constructed in accordance with the teachings of the present invention, showing one method of assembling the device and stylet.
Figure 18:
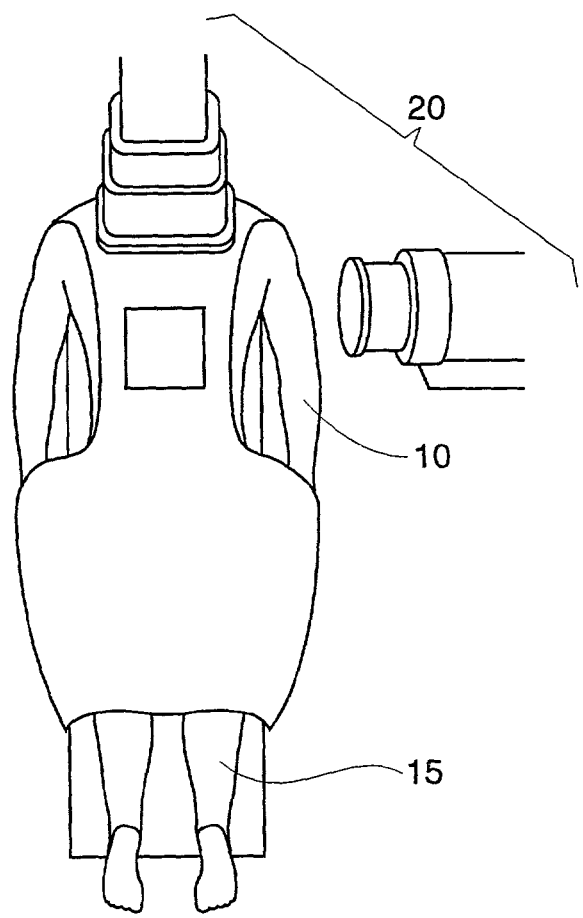
FIG. 18 depicts a patient about to undergo a surgical procedure in accordance with the teachings of the present invention.
Figure 19:
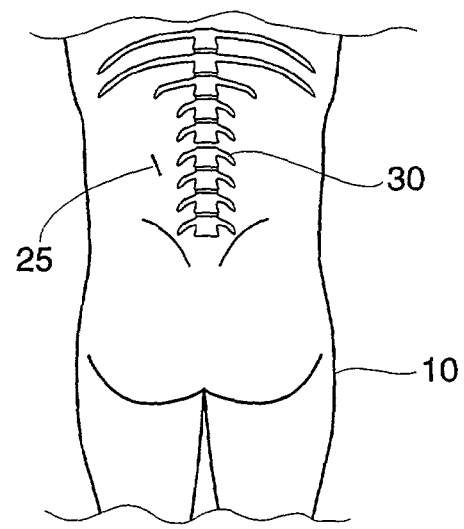
FIG. 19 depicts an incision point and underlying vertebrae for the patient of FIG. 18.
Figure 20:
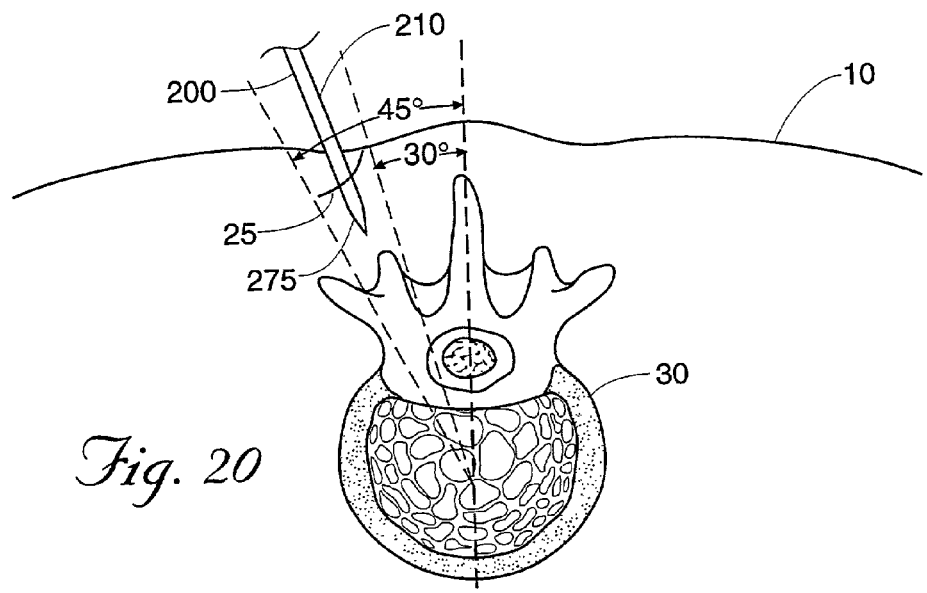
FIG. 20 is a corona view of a vertebra showing an insertion device approaching the posterior side of the vertebral body.
Figure 21A:
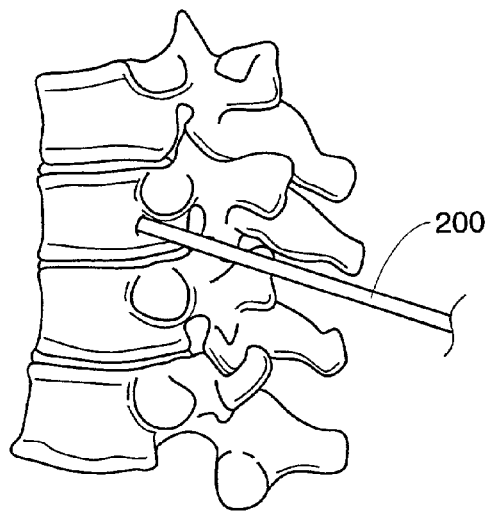
FIG. 21a depicts an insertion device penetrating the vertebral body of FIG. 20.
Figure 21B:
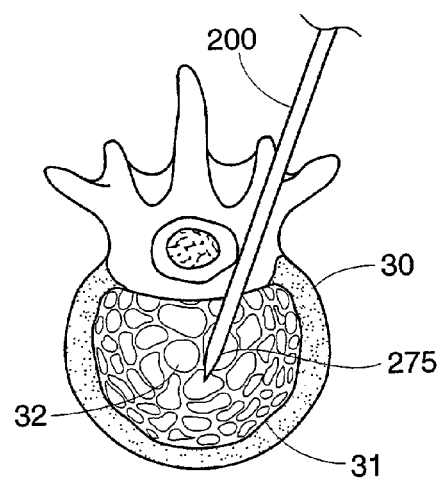
FIG. 21b is a coronal view of the vertebra of FIG. 20, with an insertion device positioned within the cancellous bone.

The insertion device of the present invention may further comprise a removable blunt obturator or stylet 275. See FIGS. 5, 9a, 9b, 12, and 17. The stylet 275 comprises a distal end 279 having a tip 276 which can be blunt or sharpened. If desired, the stylet can be cannulated (not shown) to accommodate the guide wire of a spinal needle assembly, as well known in the art. In one embodiment of the present invention, best shown in FIGS. 15, 16a and 17, the tip 276 of the stylet 275 will desirably extend from the distal end 250 of the hollow member 210 when the insertion device is assembled for insertion into an interior body region. The stylet 275 desirably pushes and/or cuts a tunnel or passageway through soft tissue and bone to permit placement of the insertion device into the desired interior body region. If desired, the stylet 275 can further comprise a mating end (not shown) which allows the boring member 275 to be mated to the insertion device during the insertion procedure, in a manner well known in the art. Mating of the hollow member 210 to the stylet 275 desirably prevents slippage and relative movement between these devices during insertion into the patient. The stylet 275 is preferably mated to the hollow member 210 in a manner which allows for easy removal of the stylet 275 from the hollow member 210 after placement of the insertion device in the targeted area.

The stylet 275 may be made of any appropriate medical grade material and is preferably made of the same material as the hollow member 210. In one preferred embodiment, the stylet 275 is made of stainless steel. The stylet 275 may further be any appropriate shape and size which allows it to slide within and mate with the hollow member 210. In a preferred embodiment, the stylet 275 is approximately the same cylindrical shape as the hollow member 210, is slightly longer than the hollow member 210 so that the tip 276 will protrude from the distal end 250 of the hollow member 210 when assembled for insertion, and is slightly smaller in diameter than the inner bore diameter of the hollow member 210, such that the stylet 275 can freely slide within the hollow member 210 for easy insertion and withdrawal.

Figure 5:
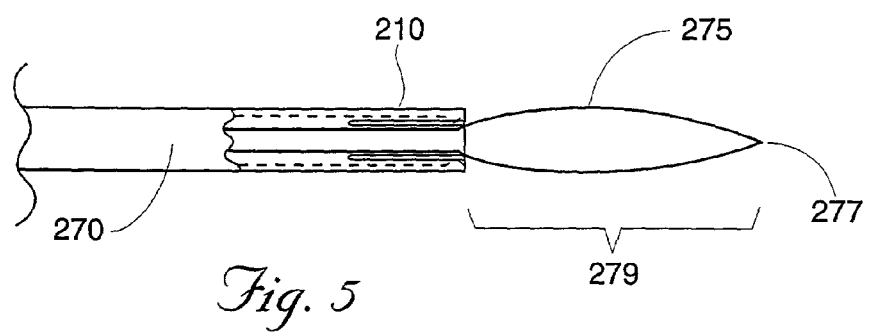
FIG. 5 is a cross-sectional side view of the insertion device of FIG. 3a, with a stylet positioned within the hollow member of the device.
Figure 3B:
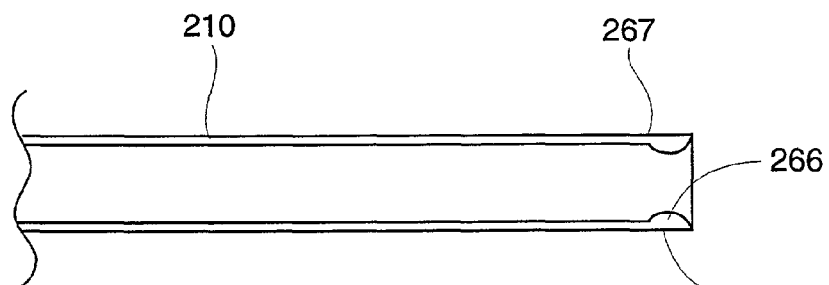
FIG. 3b is a cross-sectional side view of the insertion device of FIG. 3a, showing the adjacent sections in a lower profile orientation.
Figure 16B:
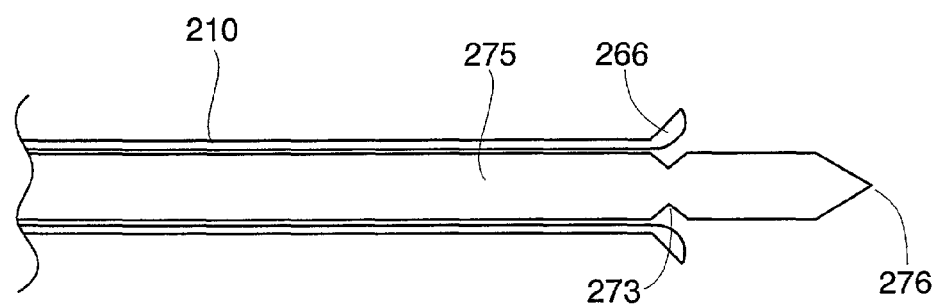
FIG. 16b is a cross section side view of the insertion device and stylet of FIG. 16a, showing the stylet inserted fully into the hollow member of the device during assembly.
Figure 17:
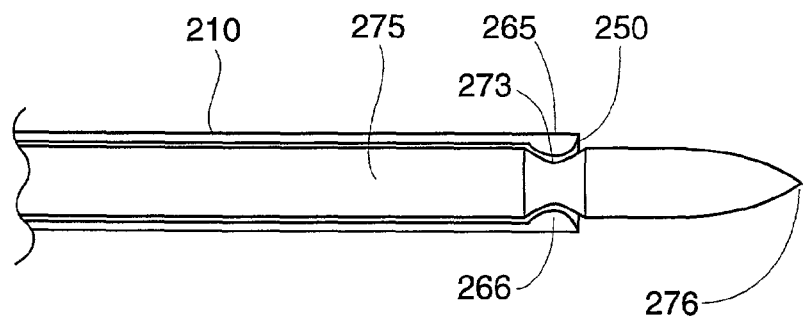
FIG. 17 is a cross sectional side view of the insertion device and stylet of FIG. 16b, with the adjacent sections of the device positioned in a lower profile orientation around the stylet.

In one embodiment of the present invention, shown in FIGS. 15, 16a, 16b and 17, the distal end 279 of the stylet 275 desirably comprises one or more grooves or divots 273 located near the tip 276. In a preferred embodiment, the divot 273 is a continuous divot which encircles the circumference of the distal end 279 of the stylet 275. A stylet 275 having at least one divot 273 at the distal end 279 is well suited to mate with a hollow member 210 having a plurality of longitudinal score lines 260 and one or more protrusions 266 on each adjacent section 265 in its distal end 250, as depicted in FIGS. 3b, 5, and 17. When such an insertion device is assembled, the stylet 275 can be inserted into the hollow member 210 until the distal end 279 extends out of the hollow member 210. The adjacent sections 265 are then folded or crimped inwards, with the protrusions 266 extending into the divot 273 in the stylet 275, such that the outer wall of hollow member 210 is relatively cylindrical prior to insertion of the insertion device. Once the insertion device is in place within the desired interior region of a body, the stylet 275 is pulled out of the hollow member 210, flaring the one or more protrusions 266 and forcing the distal end 279 of the stylet 275 outward. In another embodiment, the collar section 267 adjacent to one or more protrusions 266 is thinner than the rest of the wall of hollow member 210 to make flaring of the distal end 250 easier.

Figure 9B:
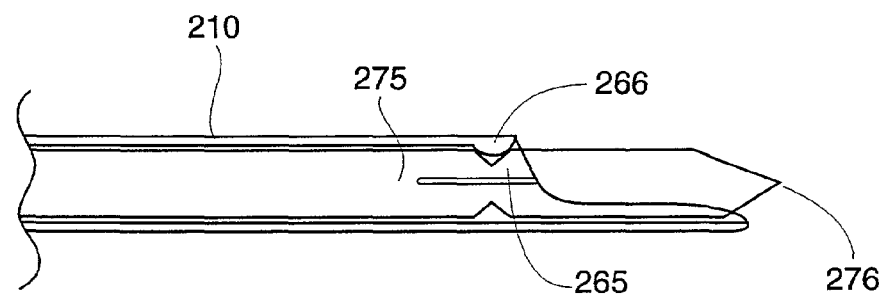
FIG. 9b is a cross sectional side view of the insertion device of FIG. 9a, showing the adjacent sections in a lower profile orientation.
Figure 9C:
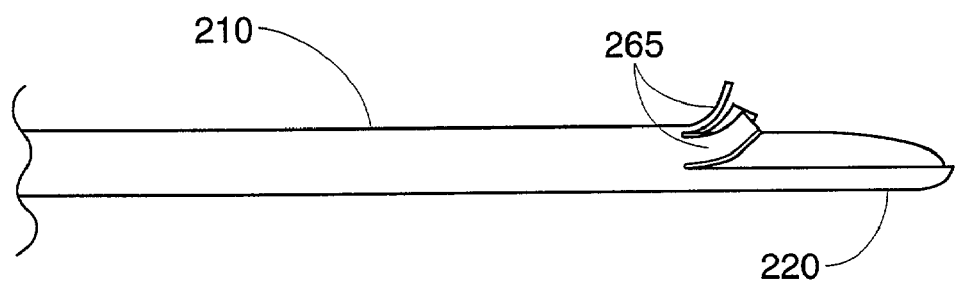
FIG. 9c is a side view of the insertion device of FIG. 9a, showing the adjacent sections moved to a deployed position as the stylet is withdrawn from the device.

In another embodiment of an insertion device constructed in accordance with the teachings of the present invention, best depicted in FIGS. 9a through 9c, an insertion device comprises a hollow member 210 having a platform 220 and one or more adjacent sections separated by a plurality of longitudinal score lines 260 at the distal end 250. In another embodiment, this type of insertion device further comprises a stylet 275 which has at least one divot 273 located near the tip 276. The stylet 275 can be used to exert outward pressure on one or more protrusions 266 on adjacent sections 265 causing the distal end 250 to flare out near the platform 220. Such a preferred embodiment of an insertion device of the present invention allows a user to direct expansion of an expandable structure, such as a medical balloon, while easing insertion and removal of the expandable structure and reducing the risk of damage to the expandable structure.

The present invention further provides methods for using the disclosed insertion devices to direct expansion of the expandable structure and/or to simplify insertion and removal of an expandable structure from an interior region of a human or animal body. For illustrative purposes, a method for osteoporotic vertebral fixation, i.e. insertion and expansion in a vertebral body, will be described. However, a similar method may be used within any appropriate region of a human or animal body.

Figure 22:
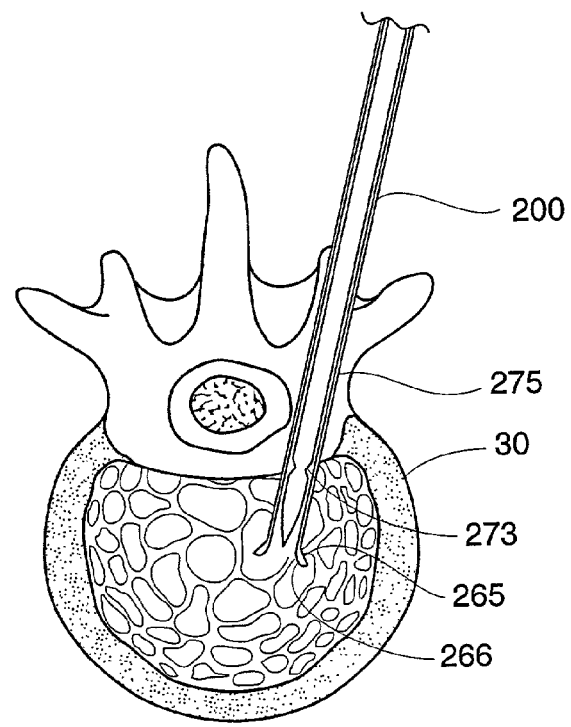
FIG. 22 is a coronal view the vertebra body of FIG. 21a, with the adjacent sections positioned in a deployed orientation.
Figure 23:
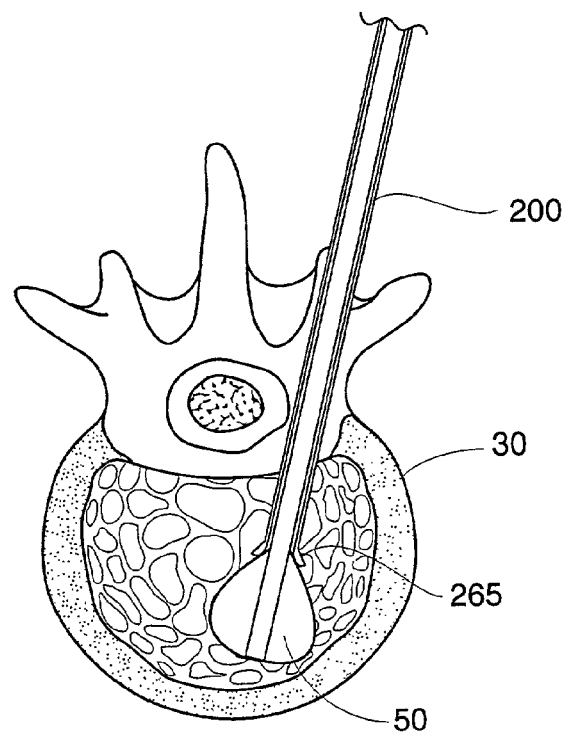
FIG. 23 is a coronal view of the vertebra body of FIG. 22, wherein an expandable structure is expanded within the vertebra.
Figure 24:
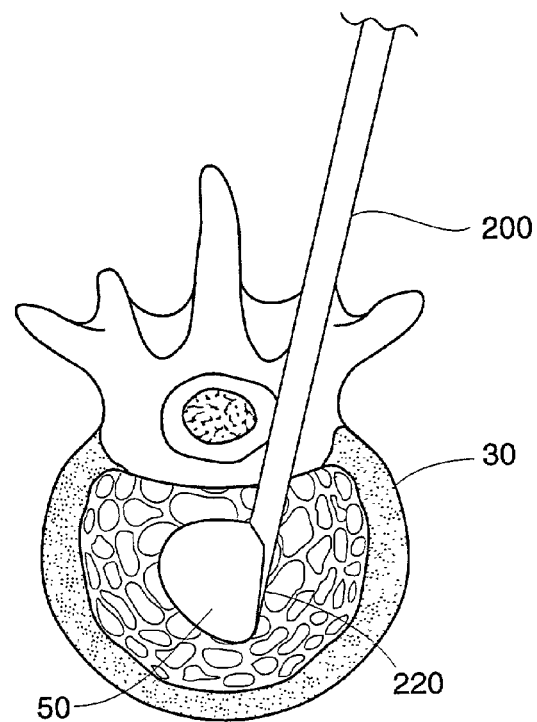
FIG. 24 is a coronal view of a vertebra showing an insertion device comprising a platform within the vertebra, and an expandable structure expanding away from the platform of the insertion device.

As shown in FIGS. 18-27, in one embodiment of the present invention, a patient 10 is placed onto a holder 15, generally U shaped, so that the patient's back is exposed. An x-ray, CAT-scan, MRI, fluoroscope, or other appropriate device 20 which permits a practitioner to visualize the insertion and placement of an insertion device during the surgical procedure may be positioned around the patient. An insertion device 200 comprising a hollow member 210 fitted with a stylet 275, as previously described above, can be introduced through the soft tissues to a vertebral body, which can located fluoroscopically. The stylet and insertion device will desirably penetrate through the cortical bone 31 of the vertebral body 30, and the stylet 275 can then be removed. In an embodiment of the insertion device wherein the hollow member 210 comprises one or more adjacent sections 265 separated by a plurality of longitudinal score lines 260, the removal of the stylet 275 desirably causes the distal end 250 of the hollow member 210 to flare as depicted in FIG. 22.

An expandable structure 50, such as a medical balloon, can be inserted through the hollow member 210 into the vertebral body 30. Placement of the expandable structure 50 can be monitored by any appropriate means, including x-ray fluoroscopy or real time MRI. The structure is expanded, creating a cavity 55 within the cancellous bone 32 and/or moving cortical bone 31, and then contracted. In an embodiment where the distal end 250 of the hollow member 210 has been flared, the flared end guides the structure 50 into the hollow member 210. The cavity 55 can then be filled with an appropriate bone filler 60.

Figure 25:
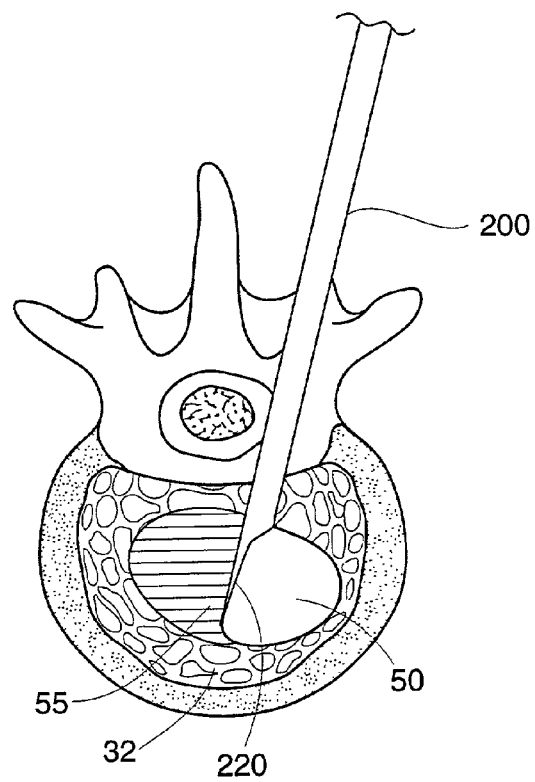
FIG. 25 is a coronal view of the vertebra of FIG. 24, wherein the expandable structure has been contracted, the device rotated, and an expandable structure expanded towards another region of the vertebra.
Figure 26:
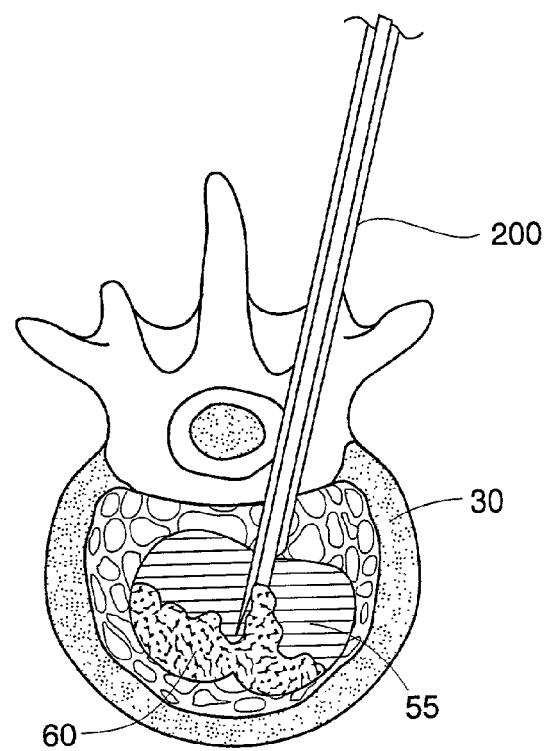
FIG. 26 is a coronal view of the vertebra of FIG. 24, wherein the created cavity is filled with a bone filler.
Figure 27:
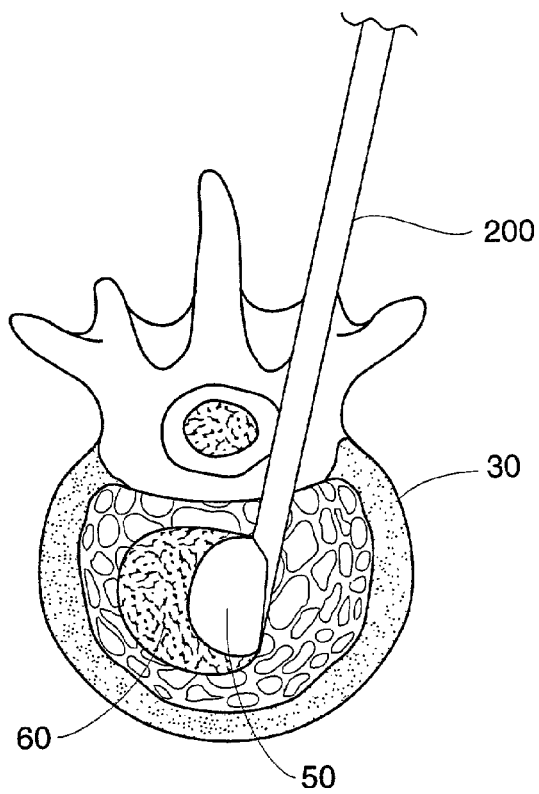
FIG. 27 is a coronal view of the vertebra of FIG. 24, wherein an expandable structure and insertion device are used to enlarge a first cavity which has been partially filled with a bone filler.

In another preferred embodiment of the present invention, the hollow member 210 comprises a platform 220 extending from the distal end 250. See FIGS. 24 through 27. Once the hollow member 210 is introduced into the vertebral body 30, the hollow member can be rotated until the platform 220 shields an area of the vertebral body where expansion of the structure 50 is undesired. When the structure 50 is expanded, the platform 220 induces the structure 50 to expand away from the platform 220. In this way, an appropriate area for a cavity may be formed generally irrespectively of where the insertion device is placed within the vertebral body. Thus, if the insertion device is placed in a position within the vertebral body that is not optimal for cavity formation, instead of torquing, bending, or otherwise adjusting the placement of the entire insertion device, the insertion device 200 may simply be rotated until the platform 220 faces a desired direction of cavity formation. An indicator (not shown) on the handle or proximal portion of the hollow member 210 will desirably indicate to the practitioner the orientation of the platform within the bone. Similarly, if a larger or asymmetrical cavity is desired, after a first cavity is formed by expanding the structure 50, the structure 50 may be contracted, the insertion device 200 may be rotated until the platform 220 faces another direction, and the same or a different structure 50 may be expanded to form a second cavity, etc., as depicted in FIG. 25. Any desired number and/or dimension of cavities may be formed in this way. In another embodiment, different shaped balloons may be inserted to form each different cavity or multiple expandable structures of varying shapes may be used to form each cavity.

When the desired cavity or cavities 55 have been formed, the expandable structure 50 may be contracted and removed through the hollow member 210. In an embodiment wherein the distal end 250 of the hollow member 210 is flared, removal of the contracted structure may be easier because the flared tip guides the structure into the hollow member 210. A suitable bone substitute, such as polymethylmethacrylate bone cement, a two-part polyurethane material, or any other appropriate bone filler 60, is injected into the cavity 55 or cavities formed. In one embodiment, a first cavity 55 may be formed and, if desired, at least partially filled with a bone filler 60, then the same or a different expandable structure 50 may be inserted and expanded in the same cavity 55, thereby compacting the hardening bone filler and/or more cancellous bone 32, and the cavity 55 may then be further filled with the same or a different bone filler 60. In another embodiment, a first cavity 55 may be formed, an insertion device 200 with a platform 220 may then be rotated and the same or a different expandable structure 50 may be inserted to create a second cavity or enlarge the first cavity 55, and the cavity(ies) may then be filled with the same or a different bone filler 60. These methods may be followed until all desired cavities have been formed and filled.

Once all desired cavities have been filled, the insertion device 200 may be removed from the vertebral body 30. The incision 25 may then be stitched closed and/or covered with bandages.

Figure 32:
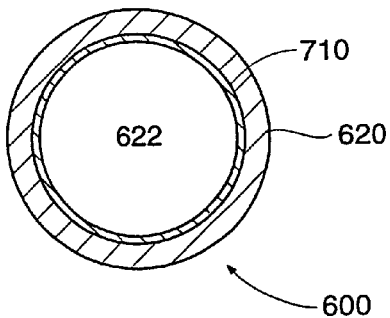
FIG. 32 is a cross-sectional view of the insertion device of FIG. 31, taken along line 32-32.
Figure 31:
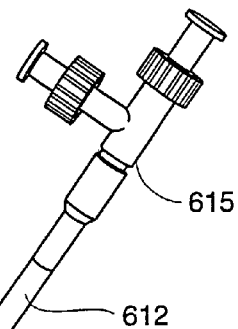
FIG. 31 is a side view of another alternate embodiment of an insertion device constructed in accordance with an alternate embodiment of the present invention.
Figure 31:
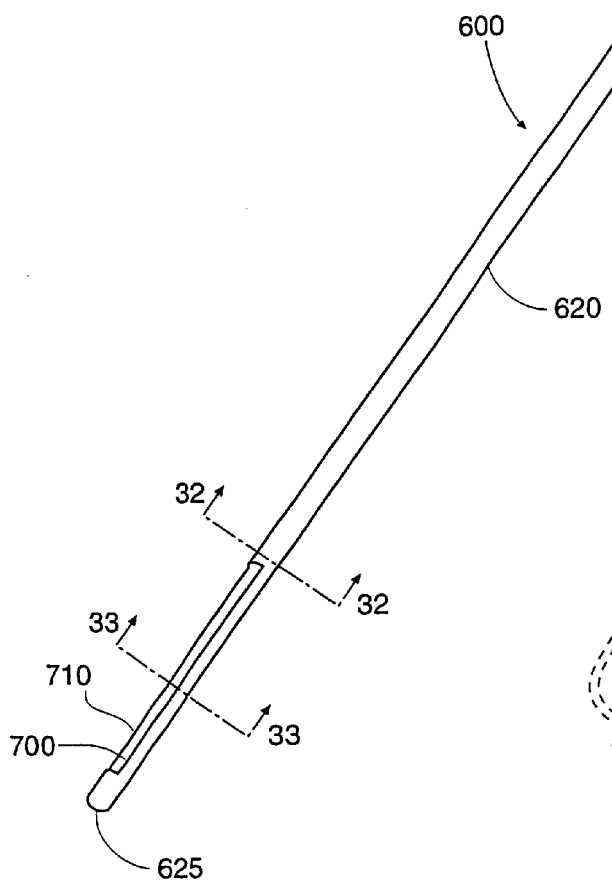
Figure 33:
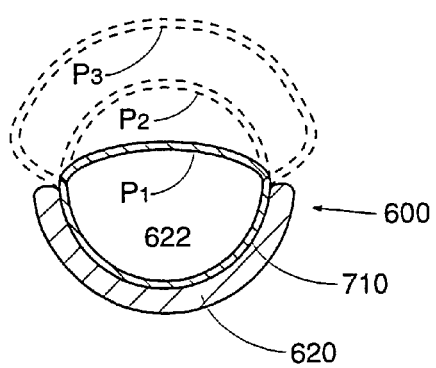
FIG. 33 is a cross-sectional view of the insertion device of FIG. 31, taken along line 33-33.

FIGS. 31-33 depict an alternate embodiment of an insertion device 600 constructed in accordance with the teachings of the present invention. The insertion device 600 comprises a hollow member 620 and an expandable structure 710. A handle 615 may be provided on the distal end of the hollow member 620 to facilitate manipulation of the tool and/or introduction of a medium to expand the expandable structure 710. The hollow member 620, desirably having a lumen 622 extending therethrough, comprises a shaft 624 and a distal tip 625. The distal end 625 of the shaft 624 can be rounded or beveled to facilitate passage through cortical/cancellous bone, or can be or flattened to minimize opportunities for penetrating the opposite cortical wall of the targeted bone region. An opening or window 700 is formed in the shaft 624, with an expandable structure 710 desirably positioned within the lumen 622 at a location adjacent the window 700. Upon introduction of the insertion device 600 into a targeted bone region (not shown), the expandable structure 710 can be expanded (See FIGS. 33, P1 to P2 to P3), and at least a portion of the expandable structure 710 will desirably expand through the window 700, thereby compressing cancellous bone, creating a cavity and/or displacing cortical bone. Upon contraction of the expandable structure 710, most of the expandable structure 710 will desirably be drawn back into the lumen 622 for removal of the device 600 from the vertebral body. If desired, the handle 615 and/or proximal end 612 of the hollow member 620 can include markings (not shown) which indicate the orientation of the window 700 within the targeted bone region.

The expandable structure 710 may be comprised of a flexible material common in medical device applications, including, but not limited to, plastics, polyethylene, mylar, rubber, nylon, polyurethane, metals or composite materials. Desirably, the shaft 624 will comprise a material that is more resistant to expansion than the material of the expandable structure 710, including, but not limited to, stainless steel, ceramics, composite material and/or rigid plastics. In an alternate embodiment, similar materials for the expandable structure 710 and shaft 624 may be used, but in different thickness and/or amounts, thereby inducing the expandable structure 710 to be more prone to expansion than the shaft 624. The expandable structure 710 may be bonded directly to the shaft 624 by various means well known in the art, including, but not limited to, means such as welding, melting, gluing or the like. In alternative embodiments, the expandable structure may be secured inside or outside of the shaft 624, or a combination thereof. In at least one alternative embodiment, at least a portion of the material comprising the expandable structure 710 will plastically deform as it expands.

If desired, the shaft 624 may be sized to pass through the lumen of a cannula or spinal access needle (not shown) already positioned within the targeted bone region. Alternatively, this embodiment of an insertion device 600 can be utilized without an associated insertion device. In such a case, the insertion device 600 will desirably incorporate a sharpened distal tip 625 capable of penetrating the soft tissues and cortical/cancellous bone of the vertebral body. The distal tip may be hollow or a solid construct, depending upon the desired penetration strength of the device 600. Similarly, the window 700 may extend around more or less of the periphery of the shaft 624, depending upon the size and configuration of the expandable structure 710 and the desired penetration strength of the device. For example, where the window 700 extends around approximately 25% of the shaft 624, the penetration strength of the device 600 will be significantly greater than where the window extends around approximately 75% of the shaft 624. If desired, the handle 615 can incorporate an impacting surface (not shown) to facilitate the use of an orthopedic mallet in placing the device 600 in a targeted bone region. In an alternate embodiment, after creation of the cavity, the expandable structure can be removed from the hollow member 600, allowing bone filler to be introduced into the cavity through the hollow member.

FIGS. 34 through 36 depict another alternate embodiment of an expansion guide 800 constructed in accordance with an alternate embodiment of the present invention. In this embodiment, the platform 810 comprises a semi-cylindrical section which extends from the walls of the hollow member 820. A notch 825 extends longitudinally along the platform 810. The notch 825 will accommodate a key or projection of an expandable structure (not shown), desirably securing the expandable structure to the platform 810.

Depending on the quality and strength of the surrounding cancellous and/or cortical bone, as an expandable structure expands against the platform 810, the structure can "slide off" the platform 810. In a similar manner, rotation of the platform may displace the expandable structure in an unwanted manner. Desirably, the notch 825 will secure the structure to the platform 810, preventing such occurrences. In addition, the structure may be contracted and the notch 825 used to draw the expanding structure back into proper orientation with the platform 810.

Figure 37:
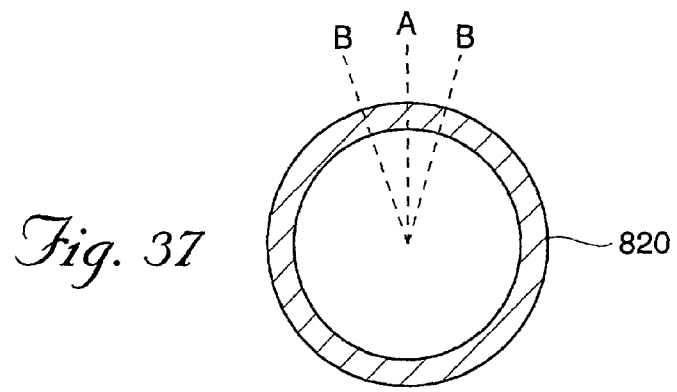
FIG. 37 is a cross-sectional view of a step in one method of manufacturing the insertion device of FIG. 34, taken along line 36-36.
Figure 38:
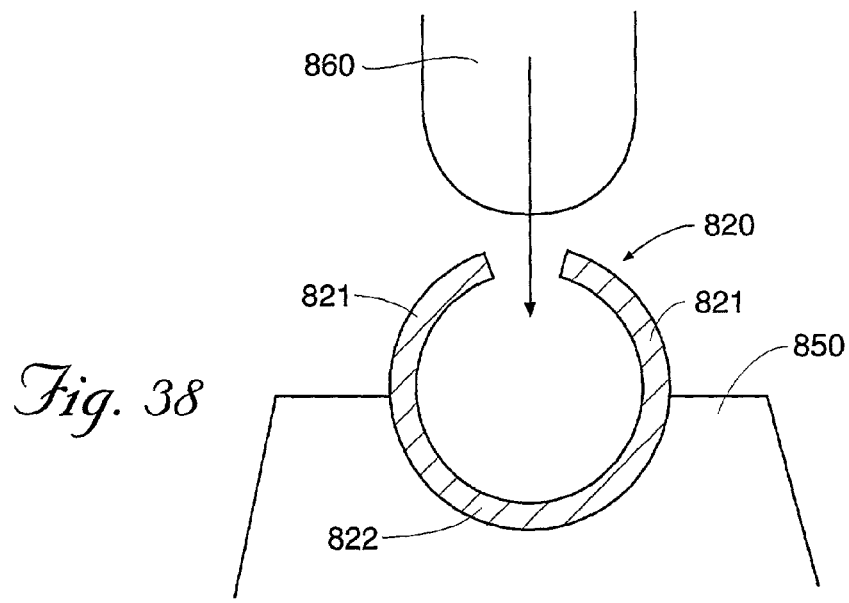
FIG. 38 is a cross-sectional view of the insertion device of FIG. 37, during a subsequent manufacturing step.
Figure 39:
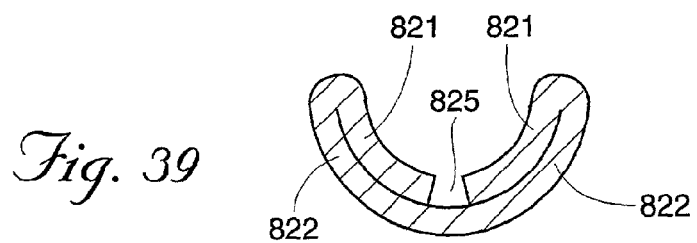
FIG. 39 is a cross-sectional view of the insertion device of FIG. 37, during a subsequent manufacturing step.

FIGS. 37 through 39 depict one method of manufacturing the platform 810 of FIG. 34. In this embodiment, a distal end of the shaft 820 is cut along a longitudinal line A. Alternatively, the shaft 820 may be cut along longitudinal lines B, depending upon the desired size of the notch and the desired angles of the side walls of the notch. The shaft is placed in a stamping machine 850 and a die 860 stamps the cut walls 821 of the shaft 820 against the opposing walls 822 of the shaft 820. Desirably, the cut walls 821 will contact the opposing walls 822, thereby forming a notch 825 between by the cut walls 821 and the opposing wall 822.

In a similar manner, a notch could be formed in the embodiment of an insertion device described in FIGS. 29 and 30, and used to guide and secure an expandable body to the platform. Once positioned within the targeted bone region, the platform could be manipulated and/or rotated with the expandable structure secured thereto. This embodiment would thereby greatly facilitate proper placement of the expandable structure on the platform in a desired orientation. If desired, the notch could be formed by molding, grinding, stamping or any other machining method known to those in the art.

While the disclosed devices and methods are more specifically described in the context of the treatment of human vertebrae, other human or animal bone types can be treated in the same or equivalent fashion. By way of example, and not by limitation, the present systems and methods could be used in any bone having bone marrow therein, including the radius, the humerus, the vertebrae, the femur, the tibia or the calcaneous.

Other embodiments and uses of the invention will be apparent to those skilled in the art from consideration of the specification and practice of the invention disclosed herein. All documents referenced herein are specifically and entirely incorporated by reference. The specification and examples should be considered exemplary only, with the true scope and spirit of the invention being indicated by the following claims. As will be easily understood by those of ordinary skill in the art, variations and modifications of each of the disclosed embodiments, including combinations thereof, can be easily made within the scope of this invention as defined by the following claims.

What is claimed is:

1. A method comprising:
providing a tool comprising a hollow body including a circumferential wall having a distal end, the tool also comprising an extension that protrudes from the circumferential wall beyond the distal end and forms a platform that is open in a radial direction to form a radial direction opening and in an axial direction to form an axial direction opening that is substantially transverse to the radial direction opening, the platform having a side surface facing in the radial direction;
providing an expandable structure;
introducing the tool and the expandable structure into a bone having an interior volume occupied, at least in part, by cancellous bone;
positioning the platform near the expandable structure, with the side surface of the platform located between the expandable structure and a first region of the cancellous bone which is not to be compressed;
securing the expandable structure to the platform in a manner to maintain a predetermined rotational orientation between the expandable structure and the platform;
forming a cavity in a second region of cancellous bone by expanding the expandable structure against the side surface of the platform with the platform serving as a barrier to induce the expandable structure to expand radially away from the side surface of the platform to compress the second region of the cancellous bone, while the first region of the cancellous bone remains substantially uncompressed, and
introducing a filler material into the cavity,
wherein forming the cavity in the second region of cancellous bone includes expanding the expandable structure in the axial direction through the axial direction opening of the platform such that the expandable structure expands in the axial direction beyond a distal end of the platform.

* * * * *